(12) United States Patent
Nicholson et al.

(10) Patent No.: US 6,342,634 B2
(45) Date of Patent: Jan. 29, 2002

(54) CALIXARENES AND THEIR USE FOR SEQUESTRATION OF METALS

(75) Inventors: Graeme P. Nicholson; Mark J. Kan; Gareth Williams; Michael G. Drew, all of Reading; Paul D. Beer, Oxford, all of (GB)

(73) Assignee: The Secretary of State for Defence in Her Brittanic Majesty's Government of the United Kingdom of Great Britain and Northern Ireland, London (GB)

( * ) Notice: Subject to any disclaimer, the term of this patent is extended or adjusted under 35 U.S.C. 154(b) by 0 days.

(21) Appl. No.: 09/880,126

(22) Filed: Jun. 14, 2001

Related U.S. Application Data

(60) Division of application No. 09/460,237, filed on Dec. 13, 1999, now Pat. No. 6,297,395, which is a continuation-in-part of application No. 09/068,148, filed on Oct. 14, 1998, now abandoned.

(30) Foreign Application Priority Data

Nov. 10, 1995 (GB) .............................................. 9523119
Nov. 4, 1996 (WO) ............................... PCT/GB96/02687

(51) Int. Cl.⁷ ............................................. C07C 233/00
(52) U.S. Cl. ....................................... 564/123; 562/405
(58) Field of Search ........................... 564/123; 562/405

(56) References Cited

U.S. PATENT DOCUMENTS

| 4,642,362 A | 2/1987 | Harris et al. |
| 4,699,966 A | 10/1987 | Harris et al. |

FOREIGN PATENT DOCUMENTS

| EP | 0 432 989 | 6/1991 |
| WO | WO 95/01346 | 1/1995 |

OTHER PUBLICATIONS

Collins, Elizabeth M. et al., "Chemically Modified Calix[4] arenes. Regioselective . . . ", Journal of Chemical Society, Perkin Transactions 1, 1991, pp. 3137–3142.

(List continued on next page.)

*Primary Examiner*—Gary Geist
*Assistant Examiner*—Hector Reyes
(74) *Attorney, Agent, or Firm*—Nixon & Vanderhye

(57) ABSTRACT

Disclosed are "acid-amide" calixarenes of formula (I) wherein: L is [—$CH_2$—] or [—O—$CH_2$—O—] and may be the same or different between each aryl group $R_5$ is H, halogen, or $C_{1-C_{10}}$ aliphatic hydrocarbyl group, $C_{6-C_{20}}$ aryl group, any of which may optionally be substituted by one or more halo or oxo groups or interrupted by one or more oxo groups, and $R^5$ may be the same or different on each aryl group; $R^1$ comprises an optionally protected carboxy group; two groups out of $R^2$, $R^3$, and $R^4$, are H; the one group out of $R^2$, $R^3$, and $R^4$ not being H comprises an amide group. The amide group may be linked to a second calixarene to form a dimer. Also disclosed are methods of use of such calixarenes for the purposes of metal sequestration, especially of lanthanides and actinides. Also disclosed are calixarene dimer derivatives of the calixarenes of the invention. Also disclosed are processes for preparing the calixarenes and dimers (I)

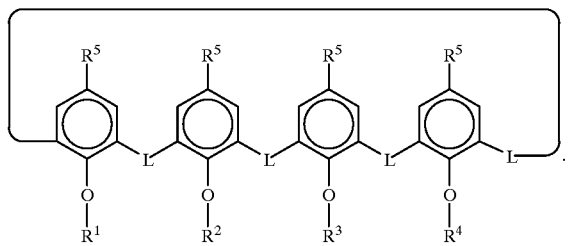

9 Claims, 13 Drawing Sheets

OTHER PUBLICATIONS

McKervey, M. Anthony et al., "A New Type of Double Calix[4]arenes by Linkage . . . ", Angewandte Chemie International Edition, vol. 29, No. 3, 1990, pp. 280–282 .

Rudkevich, Dmitry M. et al., "Calix[4]arene–triacids as Receptors . . . ", Journal of the Chemical Society, Perkin Transactions 2, 1995, pp. 131–134.

Fig.6.

CATION : ACID-AMIDE : CITRATE
1     25     3 pH=5.8-7

⊠ GOOD EXTRACTION [50-100%]

▨ PARTIAL EXTRACTION [25-50%]

☰ NO EXTRACTION [<25%]

COMPOUND 13b

COMPOUND 11b

COMPOUND 11
Rg=H:

COMPOUND 10
Rg=Me:

COMPOUND 11a

SCHEME (1)

SCHEME (2)

CALIXARENES AND THEIR USE FOR SEQUESTRATION OF METALS

This application is a division of application Ser. No. 09/460,237, filed Dec. 13, 1999, now U.S. Pat. No. 6,297,395 which is a cip of Ser. No. 09/068,148, filed Oct. 14, 1998 ABN the entire content of which is hereby incorporated by reference in this application.

The present invention relates to novel calixarenes, methods of their preparation, and uses thereof, in particular for the sequestration of metals.

European Patent Publication No. 0 432 989 describes a number of calixarene and oxacalixarene derivatives as having metal sequestering properties, and reviews some of the prior art in this field.

In a first aspect of the present invention there is disclosed calixarenes of the formula (I). The term calixarenes as used hereinafter is intended to embrace also oxacalixarenes, formula (I)

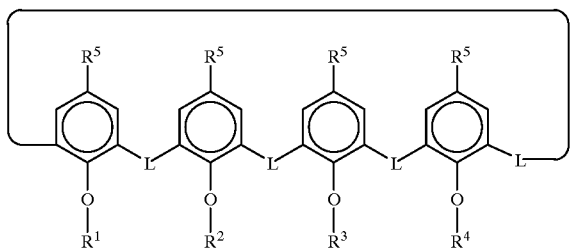

wherein:
L is [C—CH$_2$—] or [—O—CH$_2$—O—] and may be the same or different between each aryl group.
R$^5$ is H, halogen, or C$_1$–C$_{10}$ aliphatic hydrocarbyl group, C$_6$–C$_{20}$ aryl group, C$_6$–C$_{20}$ hydrocarbylaryl group, any of which may optionally be substituted by one or more halo or oxo groups or interrupted by one or more oxo groups, and R$^5$ may be the same or different on each aryl group.
R$^1$ comprises a carboxy group [—COO$^-$] which may or may not be protonated or protected. Suitable protecting derivatives include salts and ester derivatives of the carboxylic acid.
two groups out of R$^2$, R$^3$, and R$^4$ are H
the one group out of R$^2$, R$^3$, and R$^4$ not being H comprises an amide. group The combination of 'acid' (or protected acid) and 'amide' in the calixarenes of the present invention is not found in the calixarenes of the prior art; this combination leads to unexpected and desirable metal sequestering properties (particularly for lanthanide and actinide cations) as will be further discussed below.

Preferably:
R$^2$ and R$^4$ are H and R$^3$ comprises the amide group; L is [—CH$_2$—]— between each of the aryl groups;
R$^5$ is tertiary alkyl, especially butyl.
Preferably the carboxy group R$^1$ conforms to the general formula (A):

$$[—X—COOR^{10}] \quad (A)$$

wherein X is a C$_1$, a C$_2$ or a C$_3$ carbon chain being a part of an aliphatic hydrocarbyl group, aryl group or hydrocarbylaryl group, any of which may optionally be substituted by one or more halo, oxo or nitro groups.

R$^{10}$ is H or a protecting group being a salt or an Ester derivative. Salts include metal salts e.g. alkali (such as Li) or alkali earth metals, or ammonium or substituted ammonium derivatives. The choice of salt should be made such as to prevent the cation interfering with the operation of the calixarene in practice. Ester groups may be formed with C$_1$–C$_{10}$ aliphatic alkyl alcohols, C$_6$–C$_{20}$ aryl alcohols, C$_6$–C$_{20}$ hydrocarbylaryl alcohols, any of which may optionally be substituted by one or more halo, nitro, or oxo groups or interrupted by one or more oxo groups. Examples include benzyl, p-methoxybenzyl, benzoylmethyl, p-nitrobenzyl, methyl, ethyl, butyl, t-butyl etc.

More preferably R$^1$ is of the general formula (B):

wherein n is 1, 2 or 3 and R$^6$ and R$^7$ are H or halogen and can be the same or different on each carbon.

Alternatively R$^1$ may be of the general formula (C):

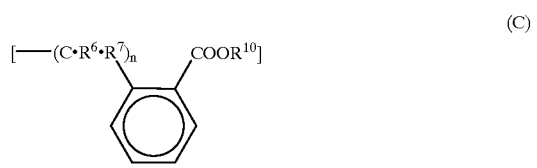

wherein n is 0 or 1 and R$^6$ and R$^7$ are H or halogen and can be the same or different on each carbon and wherein the phenyl ring of the benzoic acid group may be optionally substituted by one or more halo, oxo or nitro groups.

In each case it is preferable that a is 1 and R$^6$, R$^7$ and R$^{10}$ are all H.

In unprotected acid embodiments, preferably the aliphatic hydrocarbyl group, aryl group or hydrocarbylaryl group of X in formula (A) are substituted by one or more groups which cause a reduction in the pKa of the carboxy group with respect to the unsubstituted molecule e.g. nitro.

For instance the phenyl ring of the benzoic acid of formula (C) is preferably substituted by one or more groups which cause a reduction in the pKa of the carboxy group with respect to the unsubstituted molecule e.g. nitro.

Preferably the amide group R$^2$, R$^3$, or R$^4$ of formula (I) is of the general formula (D):

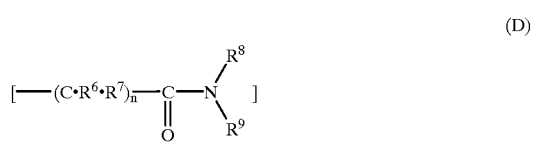

wherein n is 1, 2 or 3 and R$^6$ and R$^7$ are H, halogen, or C$_1$–C$_{10}$ aliphatic hydrocarbyl group, and can be the same or different on each carbon, and wherein R$^8$ and R$^9$, which may be the same or different, are H or C$_1$–C$_{10}$ aliphatic hydrocarbyl group (optionally halo substituted) including a cycloaliphatic ring formed by R$^8$ and R$^9$ together.

In certain embodiments of the invention, as described in more detail below, R$^8$ or R$^9$ may form a bridge to between a calixarene of the present investigation and a further calixarene in order to produce a dimer.

Most preferably, the calixarene is of the formula (II):

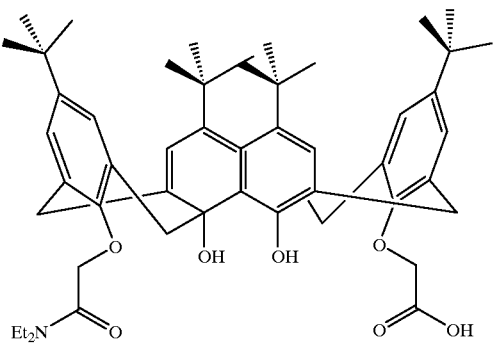

(5,11,17,23-tetra-tert-butyl-25-[hydroxycarbomylmethoxy]-27-[(N-diethylamino) carbomylmethoxy]-26-28-dihydroxy-calix[4]arene.)

This compound ("acid-amide") has been found to be useful for the extraction of both divalent and trivalent metal ions such as Pb, Sr, Hg, Bi and Y; in particular Lanthanides (e.g. La) and Actinides (e.g. U).

Also embraced by the present invention are calixarenes of the general formulae (I) and (II) but wherein some or all of the phenyl groups of the calixarene ring are further peripherally substituted in such a way as not to compromise the advantageous combination of the carboxy and amide groups which form the central core of the present invention. Possible substituents include halogen, nitro, $C_1$–$C_{10}$ aliphatic hydrocarbyl group, $C_6$–$C_{20}$ aryl group, or $C_6$–$C_{20}$ hydrocarbylaryl group, any of which may optionally be substituted by one or more halo or oxo groups or interrupted by one or more oxo groups. Indeed certain substituents (e.g. nitro) may be desirable in as much as they reduce the pKa values of the two hydroxy groups of the calixarene ring, thereby modifying the metal-chelating properties of the compound.

In a second aspect of the present invention there is disclosed a method of sequestering metals comprising contacting the metals with a calixarene as described above.

Preferably the calixarene is used to complex metals at a pH of 2–6, (most preferably pH 3–6) since at higher pHs there is an increased risk of the target metal precipitating. For instance, precipitation of Lanthanides occurs at fairly low pH (7.5 for La, 6.4 for Lu).

If required, additional complexing agents (such as are well known to the skilled person) may be used to prevent precipitation of target metals. This allows the use of the calixarene at higher pHs, which will advantageously reduce protonation of the carboxy and hydroxy groups. The use of such additional complexing agents can thus raise the useful working pH range of the calixarene to the point at which the metal-calixarene complex itself an precipitates e.g. around pH 11.

The use of higher pHs (e.g. pH 7 to 10, preferably pH 9) may be particularly advantageous for increasing the concentration of negative charge in calixarenes having protected acid groups or in calixarene-dimers, which may otherwise be reduced by the protecting group or steric effects respectively.

If desired the environmental pH may be adjusted using conventional methods of the art. For instance if it is desired to raise the pH, then LiOH may be added. If desired, the pH may be buffered by using an appropriate buffer such as are well known to those skilled in this art eg. citrate.

In all cases the lower pH limit of useful operation will be dependent on the pKa of each chelating group in the calixarene, since that will dictate whether each (unprotonated) carboxy or hydroxy group will be protonated at any given pH. It may therefore be desirable for each group to have a low pKa e.g. when treating acidic waste streams for which the pH cannot be readily adjusted. The pKa of the protonated carboxy and the amide group of the calixarene of formula (II) is less than 3.

Preferably the calixarene is dissolved in a hydrophobic organic solvent (e.g. dichloromethane) and this is mixed with an aqueous phase containing metal ions (e.g. in equal volumes).

The phases are then stirred or otherwise agitated, typically for around 1 hour, followed by a 2 hour separation time.

Preferably the calixarene is present in excess over the metal target e.g. 25-fold, or 250-fold. The excess required for useful extraction will depend on the nature of the metal target e.g. size, charge etc.

Preferably the metal target is U, Hg, Am, Pb, Sr, Bi, or Y for instance in methods of environmental clean up. Alternatively the metal could be an actinide such as Am or another lanthanide.

The calixarenes described above are such that the metal complexes formed with the target ion may be overall neutral without the necessity for additional counter-anions. A further advantage is that the calixarenes can be highly selective, thereby preventing unwanted metal ions complexing all available sites.

A still further advantage of the methods of the current invention is that the extracted metal ions can be recovered following sequestration into the hydrophobic phase simply by contacting that phase with a relatively small (with respect to the original metal-containing sample) volume of acid (e.g. 1 M) thereby causing the pH to drop and the metal to become decomplexed and enter the acid aqueous phase. The calixarene can then be reused simply by evaporation of the solvent.

Alternatively, the extracted metal ions can be recovered following extraction simply by evaporating the solvent to leave the metal-calixarene complex.

Thus in preferred forms, e.g. using the 'acid-amide' above, the extraction methods of the present invention are both selective and efficient and do not require additional ions to operate. The nature of the extraction can be readily optimised by adjustment of the pH.

In a third aspect of the invention there is disclosed a solid phase-bound calixarene of the type described above e.g. polymer bound. For instance the calixarene may be physisorbed and immobilised onto polystyrene divinyl benzene beads. Immobilisation of the calixarene on a solid phase support may assist in the extraction methods of the invention. The preparation of such bound calixarenes would present no undue burden to those skilled in the art, in the light of the present disclosure in conjunction with the methods, or methods analogous to the methods, described by Harris et al. in U.S. Pat. No. 4,642,362 or 4,699,966, or Parker in U.S. Pat. No. 4,447,585 or Tetrahedron 36 461–510 (1980), or in European Patent Publication No. 0 217 656.

In a fourth aspect of the invention there is disclosed a process for preparing the calixarenes described above. Intermediates for use in the process form a fifth aspect of the invention.

In a sixth aspect of the invention there is disclosed a calixarene dimer comprising two calixarenes of formula (I) wherein the amide group of each is of the general formula (D) above, and wherein the $R^8$ or $R^9$ group of one calixarene is conjugated to the $R^8$ or $R^9$ of the other calixarene, optionally through a spacer group $R^{11}$ as shown schematically in formula (III):

formula (III)

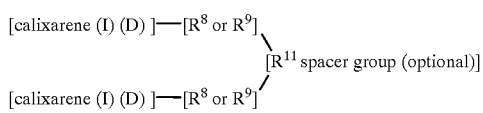

The optional spacer group $R^{11}$ may be $C_1$–$C_6$ aliphatic hydrocarbyl group, $C_6$–$C_{10}$ aryl group, $C_6$–$C_{16}$ hydrocarbylaryl group, any of which may optionally be substituted by one or more halo or oxo groups or interrupted by one or more oxo groups. In the absence of a spacer group the $R^8$ or $R^9$ group of one calixarene is conjugated directly to the $R^8$ or $R^9$ group of the other. In any case it is preferable that there is only 1, 2, 3 or 4 bridging atoms (preferably carbon atoms) between the Nitrogen atoms of the two amide groups. Most preferably there is 2 or 3 bridging carbon atoms. As described in more detail below, this spacing between the calixarenes may help to pre-stress the dimer into a particular stable, low-energy, chelating conformation, and thereby enhancing the specificity for target metals with respect to calixarene monomers. groups or interrupted by one or more oxo groups. In the absence of a spacer group the $R^8$ or $R^9$ group of one calixarene is conjugated directly to the $R^8$ or $R^9$ group of the other. In any case it is preferable that there is only 1, 2, 3 or 4 bridging atoms (preferably carbon atoms) between the Nitrogen atoms of the two amide groups. Most preferably there is 2 or 3 bridging carbon atoms. As described in more detail below, this spacing between the calixarenes may help to pre-stress the dimer into a particular stable, low energy, chelating conformation, and thereby enhancing the specificity for target metals with respect to calixarene monomers.

In a further aspect of the invention there is disclosed a calixarene of formula (IV):

formula (IV)

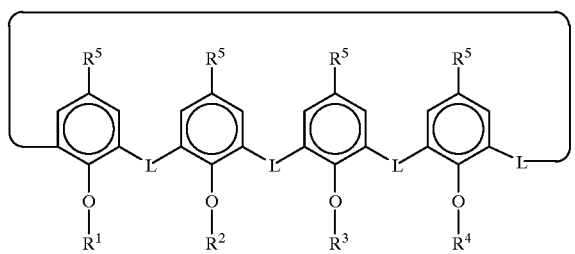

wherein:

L is [—$CH_2$—] or [—O—$CH_2$O—] and is the same or different between each aryl group; $R^5$ is halogen, or is a $C_1$–$C_{10}$ aliphatic hydrocarbyl group, $C_6$–$C_{20}$ aryl group or a $C_6$–$C_{20}$ hydrocarbylaryl group, any of which is optionally substituted by one or more halo or oxo or is interrupted by one or more oxo groups, and $R^5$ is the same or different on each aryl group;

$R^1$ is a carboxy group which is or is not protonated or protected; two groups out of $R^2$, $R^3$ and $R^4$ are H; and the one group out of $R^2$, $R^3$ and $R^4$ which is not H is a thioamide group.

In a preferred embodiment $R^2$ and $R^4$ are H, $R^5$ is the same on each aryl group and is a

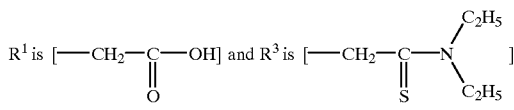

Alternatively, $R^2$ and $R^4$ are H, $R^5$ is the same on each aryl group and is a tertiary

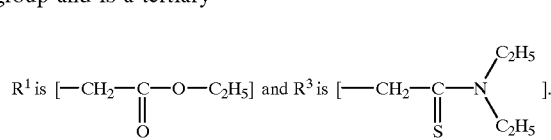

In another embodiment of the invention there is disclosed a method for preparing the calixarenes of formula (IV) above.

Furthermore, there is described a method for the sequestration of metals comprising contacting the metals with a calixarene of formula (IV) as described above.

The compounds, methods and processes of the present invention will now be described, by way of illustration only, through reference to the following Figures ad Examples. Other embodiments falling within the scope of the invention will occur to those skilled in the art in the light of these.

FIGURES

FIG. 6 shows the efficiency of extraction of various metals by acid-amide in the presence of buffer (citrate).

Figure 12:
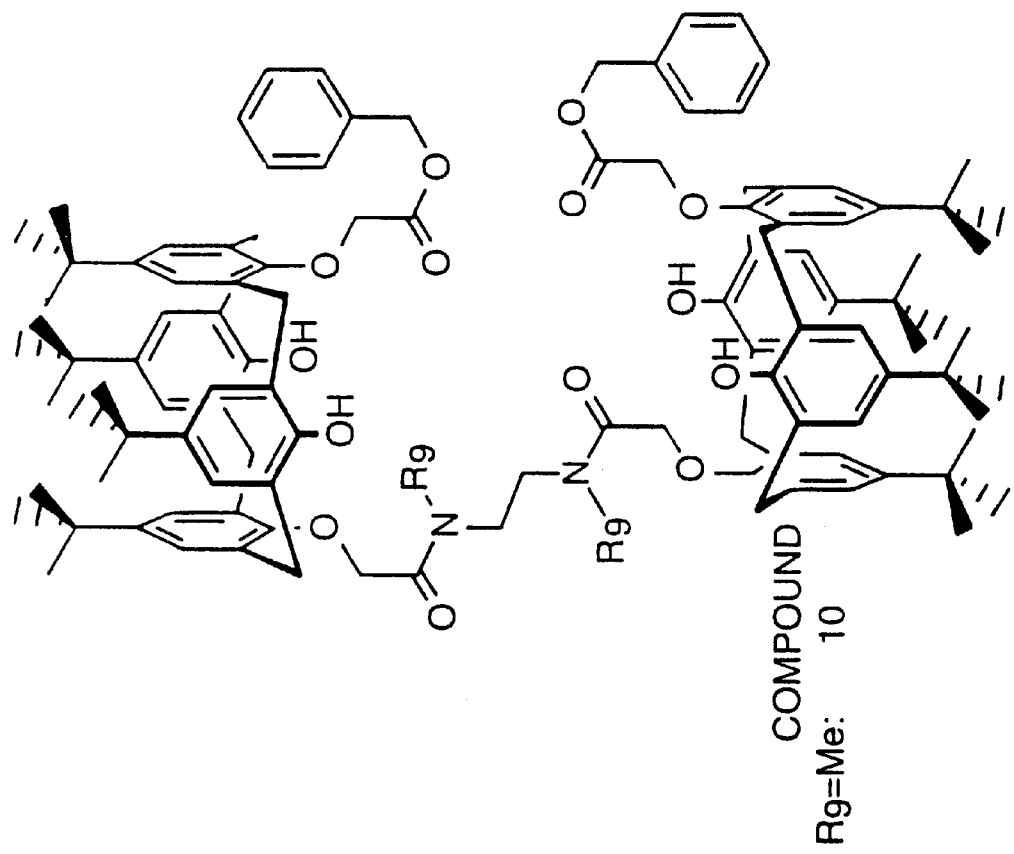

FIG. 12 shows a calixarene dimer (designated 10) according to the present invention wherein the carboxy groups of the calixarenes have been protected by esterification with benzyl alcohol. The Nitrogen atoms of the two amide groups are linked via a 2-C ethyl bridge. The tertiary group of the Nitrogens (designated $R^9$) is methyl in each case.

Figure 13:
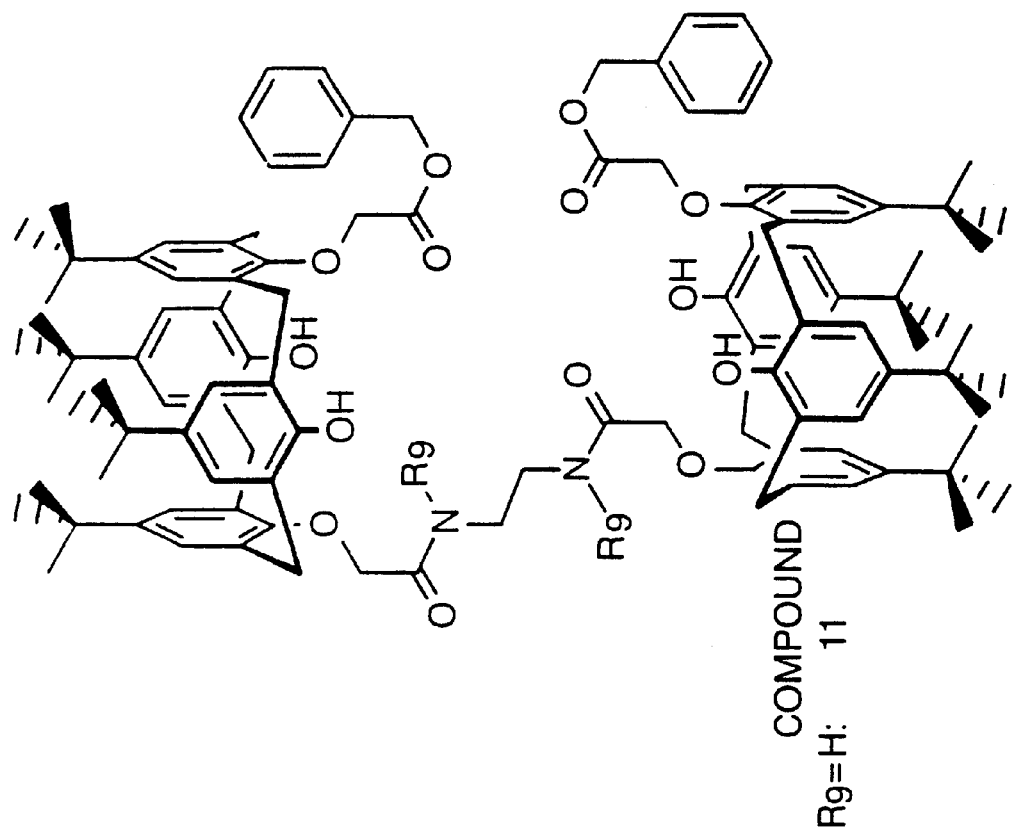

FIG. 13 shows a calixarene dimer (designated 11) according to the present invention wherein the carboxy groups of the calixarenes have been protected by esterification with benzyl alcohol. The Nitrogen atoms of the two amide groups are linked via a 2-C ethyl bridge. The tertiary group of the Nitrogens (designated $R^9$) is hydrogen in each case.

Figure 14:
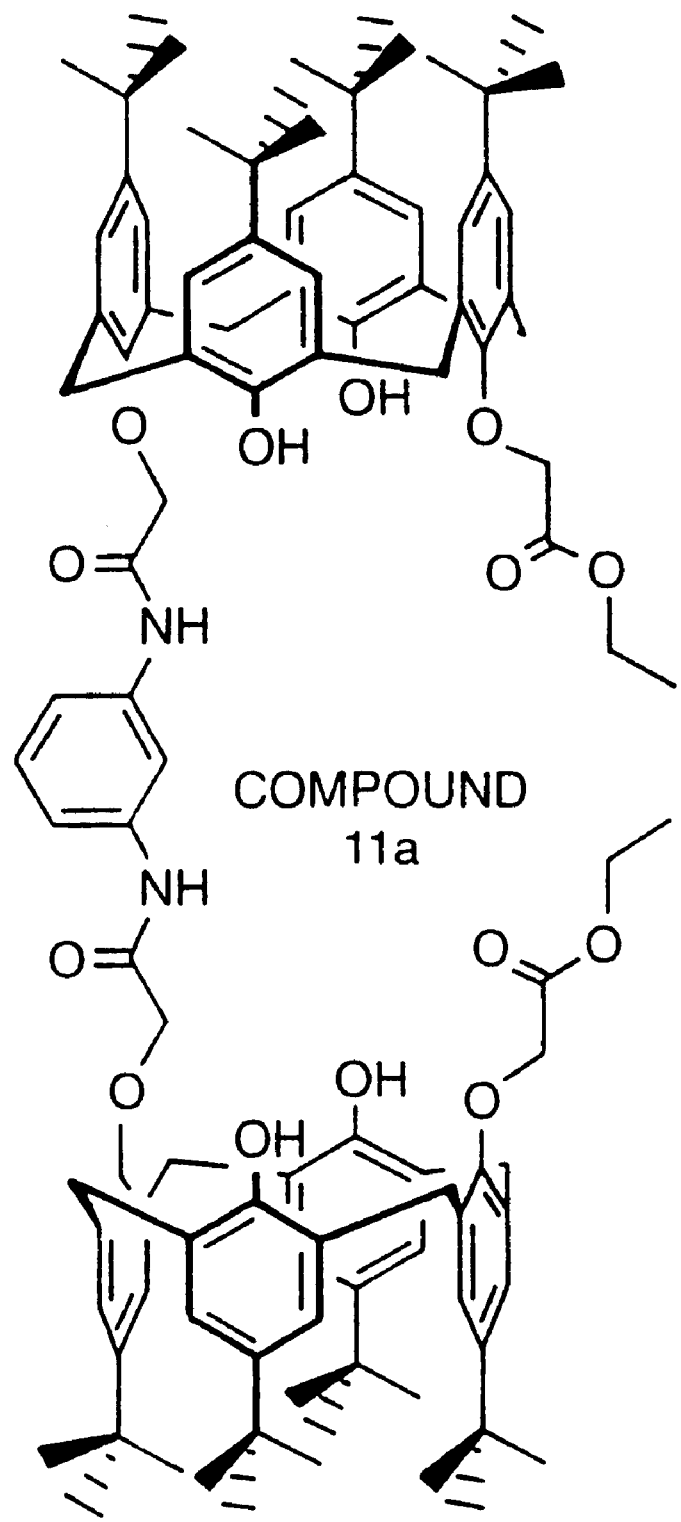

FIG. 14 shows a calixarene dimer (designated 11a) according to the present invention, wherein the carboxy groups of the calixarenes have been protected by as an ethyl ester. The Nitrogen atoms of the two amide groups are linked via a 3-C aromatic bridge. The tertiary group of the Nitrogens is hydrogen in each case.

Figure 15:
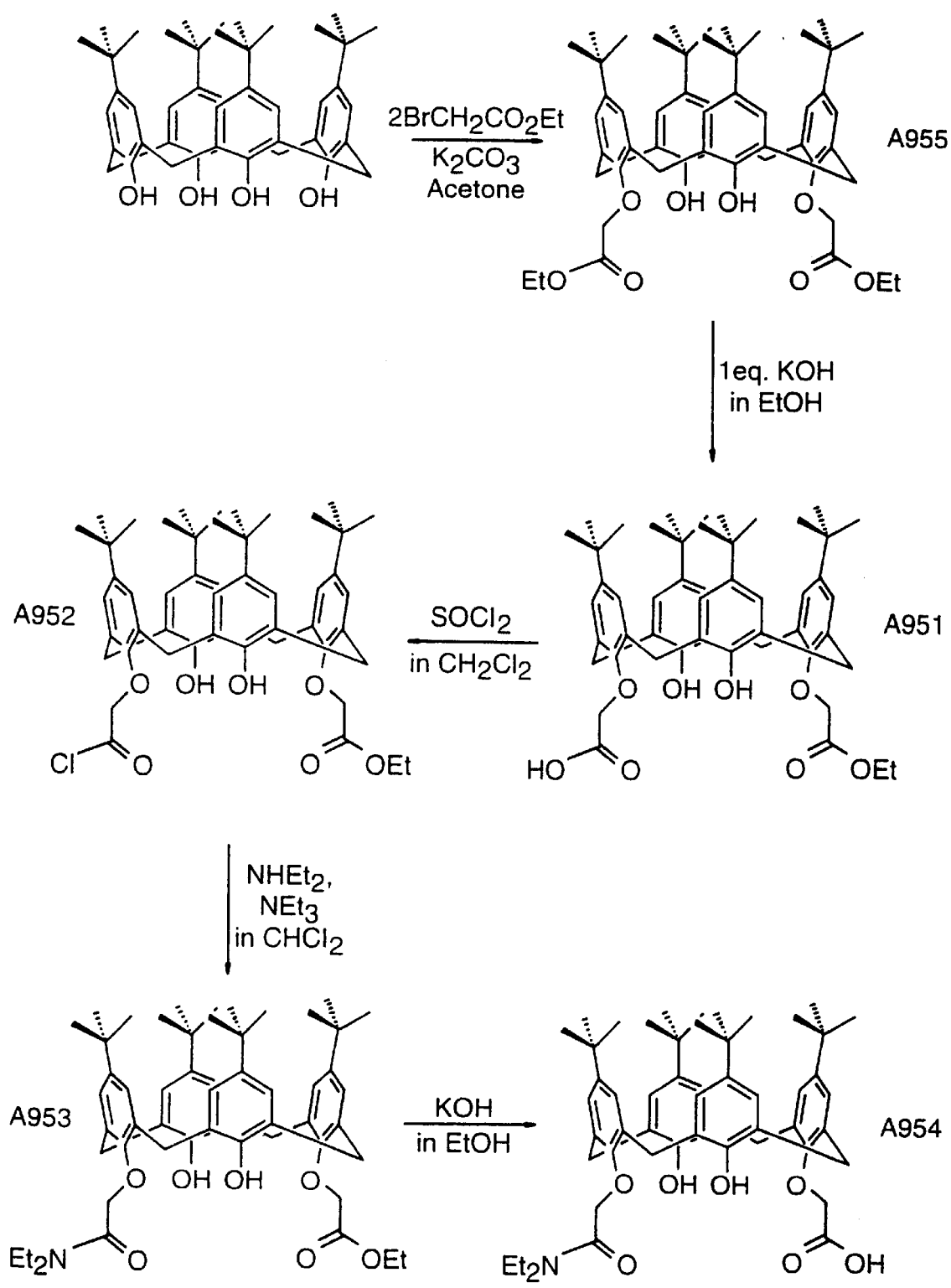

FIG. 15 shows a synthetic scheme for the acid-amide (954)

Figure 16:
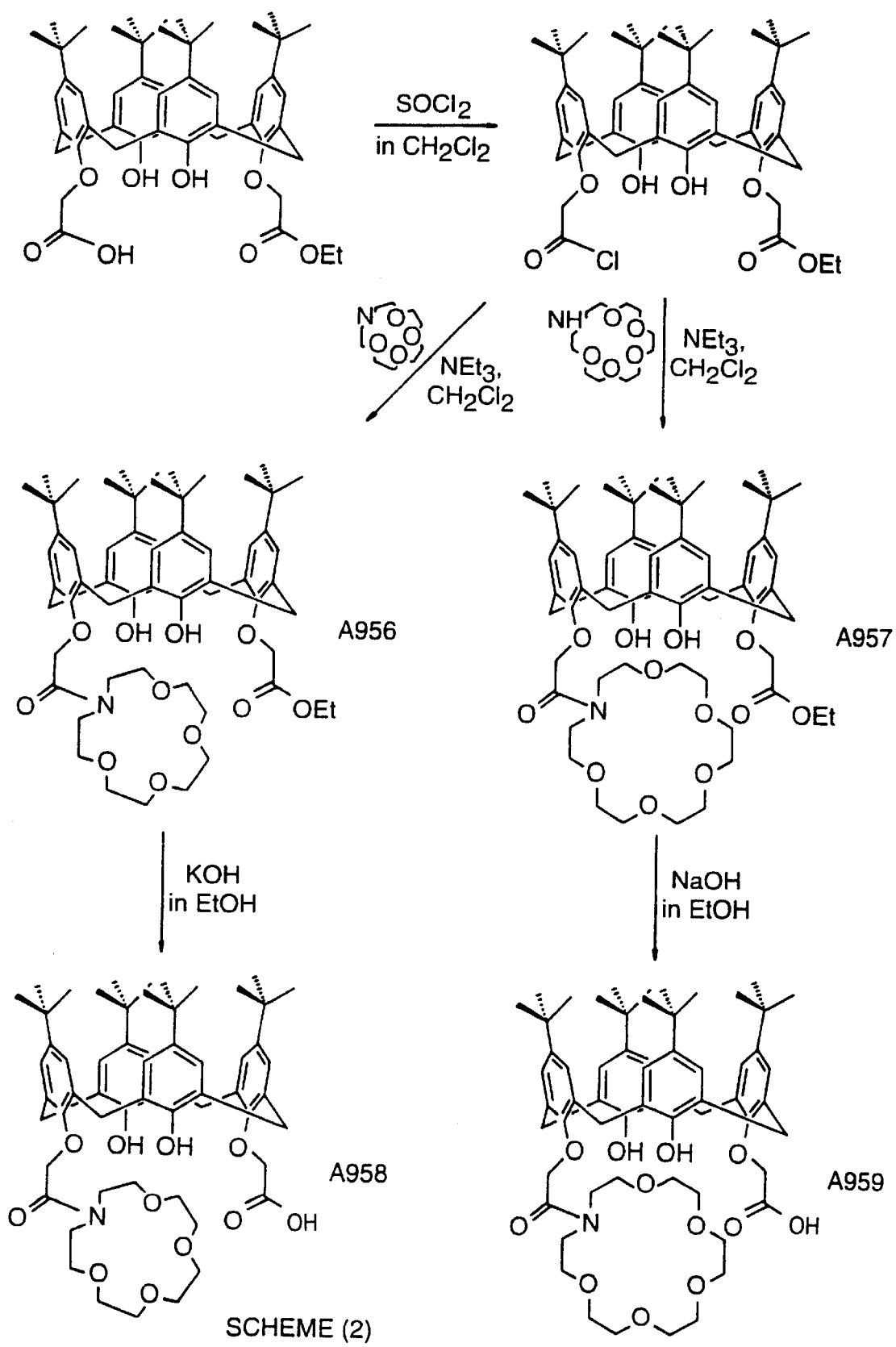

FIG. 16 shows a synthetic scheme for the azacrown-acid calix[4]arenes A957 and A959.

Figure 17:
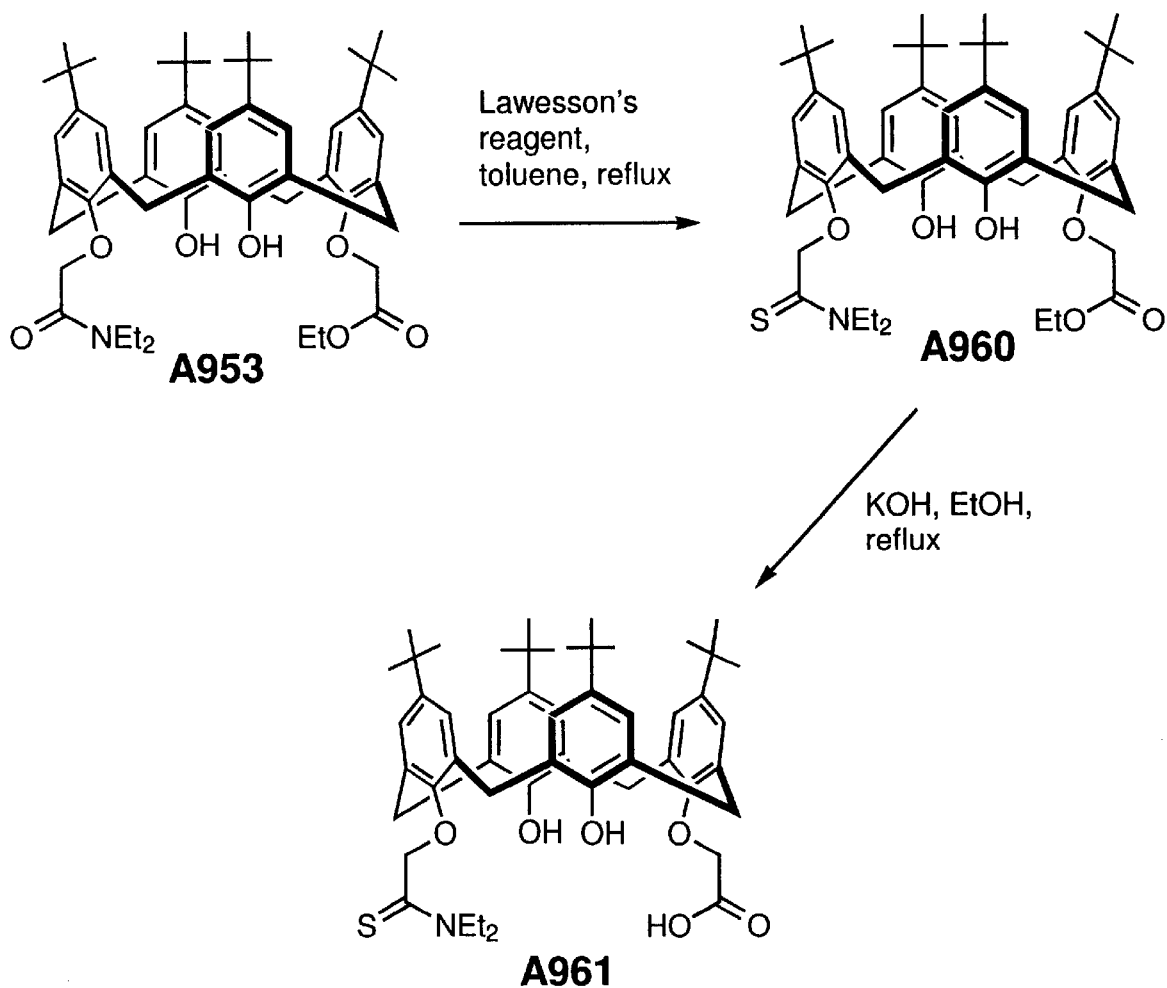

FIG. 17 shows a synthetic route for the ester-thioamide A960 and the acid-thioamide A961.

Figure 18:
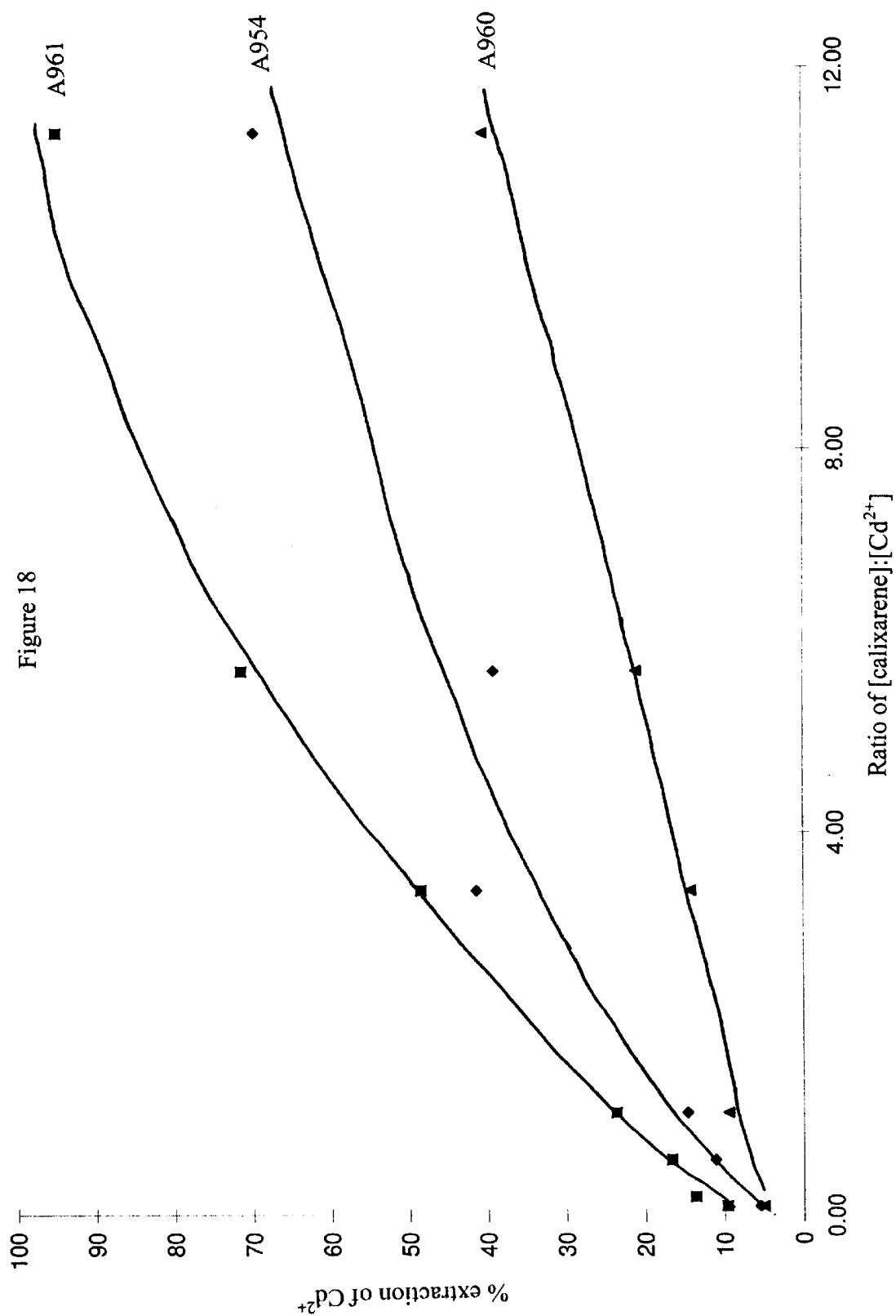

FIG. 18 shows the variation in % extraction of Cadmium (Cd) ions with the molar ratio of Calixarene:Cd for acid-amide A954, ester-thioamide A960 and acid-thioamide A961 at pH=9.4.

EXAMPLES

Example 1

The pH changes associated with the combination of various of the agents used in the later examples was first measured in order to better interpret the findings. The standard extraction of dichloromethane and aqueous phase in equal volumes with 1 hour stirring plus 2 hours separation was employed. The La (III) was used at a concentration of 0.4 mM, and the other agents were used in a ratio of 1:3:24 for La (III):citrate:acid-amide. The results, measured to +/−0.1 pH units, are shown in Table 1.

TABLE 1

| Solution type | pH before extraction | pH after extraction |
|---|---|---|
| (no agents) | 5.6 | 5.5 |
| acid-amide | 5.6 | 5.6 |
| La (III) | 5.6 | 4.9 |
| acid-amide La (III) | 5.6 | 4.9 |
| Citrate | 6.0 | 6.1 |
| Citrate acid-amide | 6.0 | 6.1 |
| Citrate La (III) | 6.0 | 6.0 |
| Citrate acid-amide La (III) | 6.0 | 6.1 |

Example 2

Figure 1:
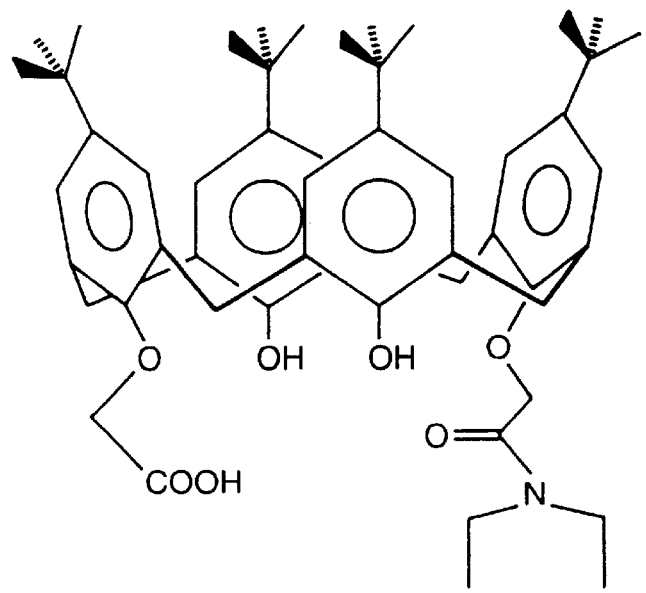
FIG. 1 shows the acid-amide of the present invention.
Figure 2:
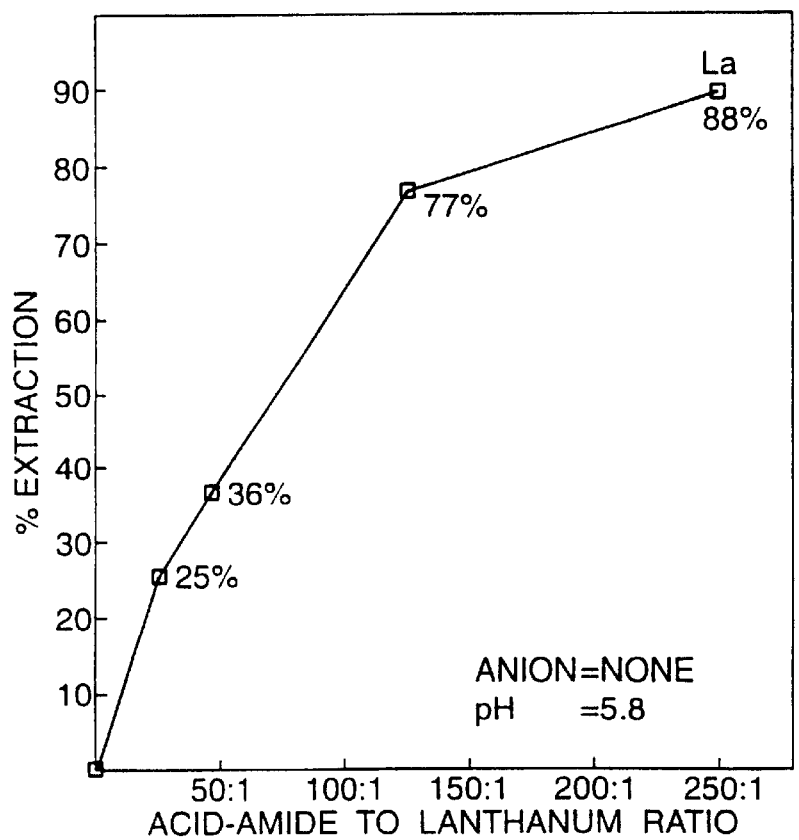
FIG. 2 shows the efficiency of extraction of La (III) by acid-amide as a function of concentration ratio of the two.

The efficiency of extraction of La (III) by acid-amide as a function of the concentration ratio of the two was measured at an initial pH of 5.8 (FIG. 2). The pH was not maintained at this level during the experiment. A result of 90% extraction was achieved using a large (250 x) excess of acid-amide. It is postulated that this large excess was required because of a drop in pH during the course of the experiment (see Example 1) which led to reduced deprotonation of the three ionizable groups. In a similar experiment using $UO_2^{2+}$ only a 25 x excess was required, possibly because as a divalant cation it can still be efficiently bound when the three ionizable groups of the acid-amide are partially protonated.

Example 3

Figure 3:
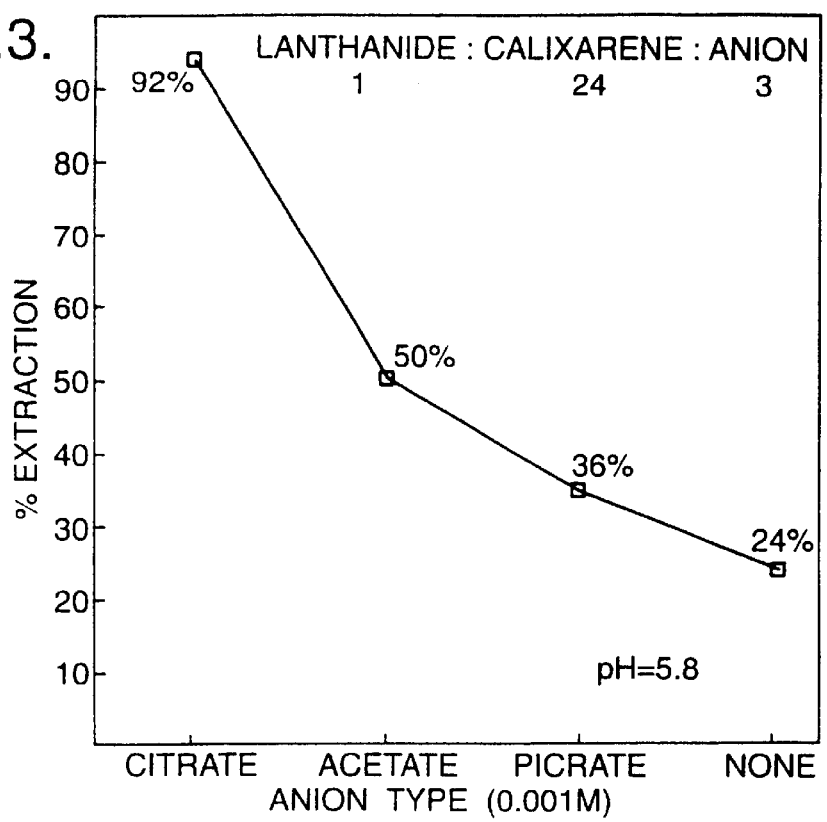
FIG. 3 shows the efficiency of extraction of La (III) by acid-amide as a function of the presence of various anions (citrate, acetate, picrate).

The effect of various anions on the efficiency of extraction is shown in FIG. 3. Citrate was found to be the best, probably because of its buffering ability. In order to demonstrate that citrate is not itself involved in the actual extraction or complexation of La (III), LiOH was titrated into the mixture to retain pH 6 instead of using a citrate buffer. The level of extraction obtained (90% La (III)) was similar to that achieved with citrate, indicating that citrate is not actually required to achieve efficient acid-amide extraction. The postulated non-coordination of the La (III) by citrate when acid-amide is present indicates a high formation constant (i.e. tight binding) for the La (III)/acid-amide complex.

Example 4

Figure 4:
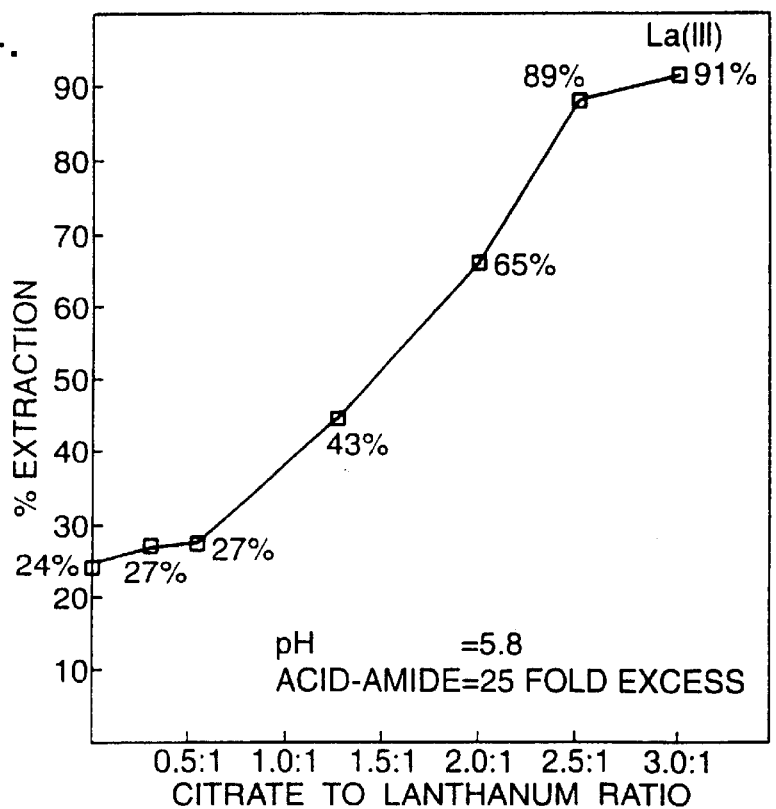
FIG. 4 shows the efficiency of extraction of La (III) by acid-amide as a function of concentration of buffer (citrate).

The optimum amount of citrate required for La (III) extraction was assessed (FIG. 4). The results indicate that a 3x excess over La (III) is suitable.

Example 5

Figure 5:
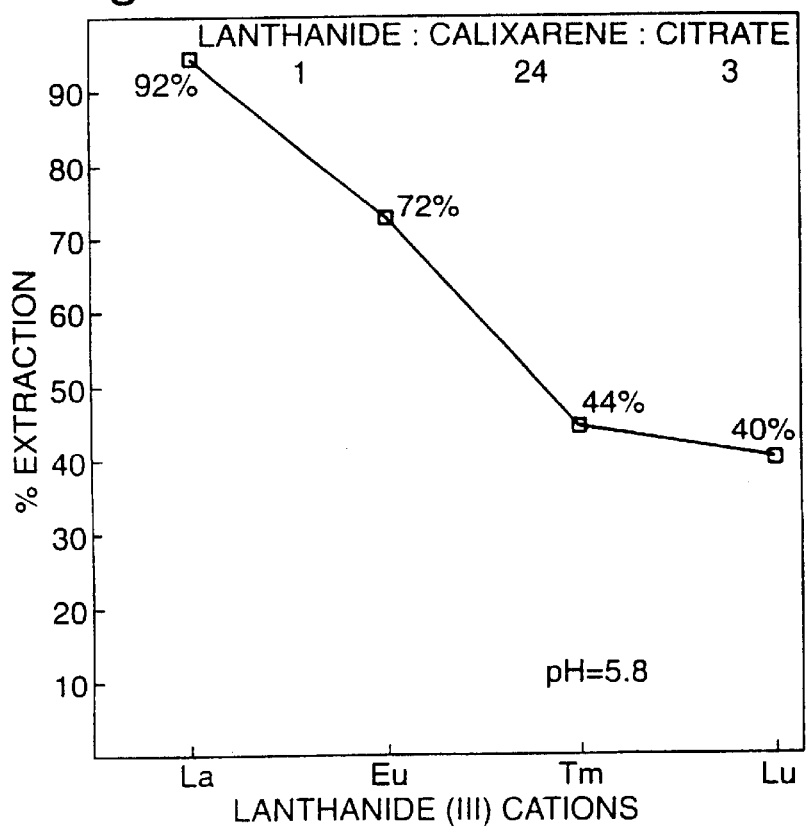
FIG. 5 shows the efficiency of competitive extraction of different Lanthanide (III) cations by acid-amide in the presence of buffer (citrate).

The efficiency of competitive extraction of various members of the Lanthanide series is shown in FIG. 5. The efficiency appears to drop off across the series, probably as a result of the change in the size of the metal cations. The results with Lanthanides indicate that it is likely certain actinides such as Am (III) will also be efficiently extracted.

Example 6

The efficiency of extraction of various metals by acid-amide in the presence of citrate was measured, the results being shown in FIG. 6. The results indicate high selectivity within the broad range of elements assessed. The extraction of La, U, Hg, Sr, Eu, Tm, Lu, Bi, and Pb is especially efficient, particularly as compared with the alkali and the smaller alkali-earth metals, and various other transition metals.

Example 7

Figure 7:
FIG. 7 shows the efficiency of extraction of various metals by acid-amide in the absence of buffer.
Figure 7:
Figure 7:
Figure 7:
Figure 7:

FIG. 7 shows the efficiency of extraction of various metals by acid-amide in the absence of buffer. As can be seen, efficiency is reduced as compared with FIG. 6 (with buffer).

Example 8

Single crystals of some metal/acid-amide complexes (Sm, Eu, Lu) were grown and analysed using X-ray crystallography. Results indicate that the intermediate Lanthanides (Sm, Eu) prefer to form a neutral dimer structure of 2 acid-amide molecules binding 2 metal ions (see FIG. 8 which shows an acid-amide/Ln (III) complex, wherein Ln=Sm or Eu). The complex is a dimer in the solid state. The acid-amide takes up the cone conformation. The Sm cations are 8 coordinate, being bound to the deprotonated phenolic oxygen atoms, the ethereal oxygen atoms, the amide oxygen and one of the carboxyl oxygens. The remaining two coordination sites are made up from a methanol oxygen and a carboxyl oxygen from the second calixarene hence forming a bridge between the two calixarenes.

Figure 9:
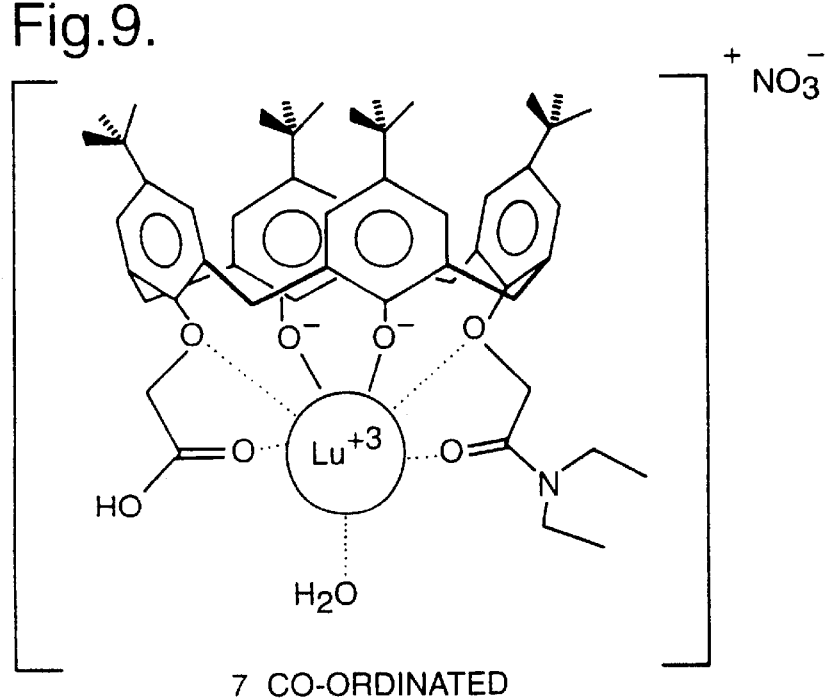
FIG. 9 shows the structure of an acid-amide/Lu (III) complex, as determined by X-ray crystallography.

Molecular modelling suggested that all the larger Lanthanides would form isomorphic structures and that only the smaller Lanthanides (Gd-Lu) would form discrete monomeric complexes. Lu (smallest Lanthanide) forms a structure with 1 acid-amide and 1 metal ion which requires a counter anion for charge neutrality. FIG. 9 shows an acid-amide/Lu (III) complex with $NO_3$ as the counter ion. The Lu cation is shown to be seven coordinate, bound to the two phenolate oxygens, the two ethereal oxygens, the amide oxygen, one carboxylate oxygen and a water molecule.

These structures may help to account for the specificity demonstrated in Examples 5 and 6.

Example 9

Metal/acid-amide complexes were further investigated by extracting the complexes from the hydrophobic phase and determining the metal:acid-amide ratio. For La, Lu and U at pH 6 the M:L ratio was 1:1. This confirms the solid-state ratios determined for the larger lanthanides and Lu by X-ray crystallography in Example 8 (which were 2:2 and 1:1 respectively). No X-ray data was obtained for U.

Example 10

Acid-amide dimers and esters thereof were prepared based on the acid-amide calixarenes of the present invention, as described in more detail in Example 15 below. Some of these are shown FIGS. 10 to 14.

Figure 8:
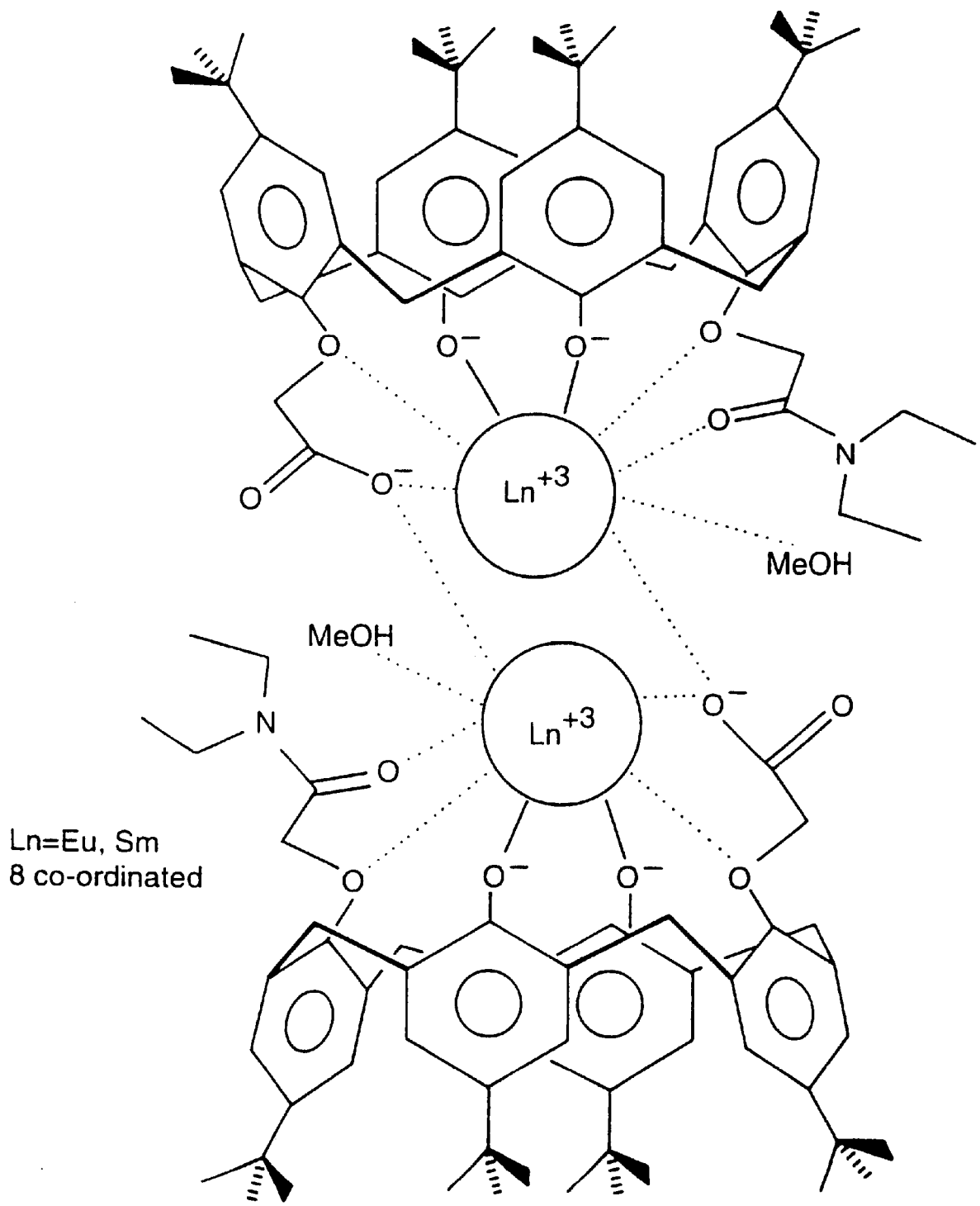
FIG. 8 shows the structure of an acid-amide/Ln (III) complex, as determined by X-ray crystallography.
Figure 10:
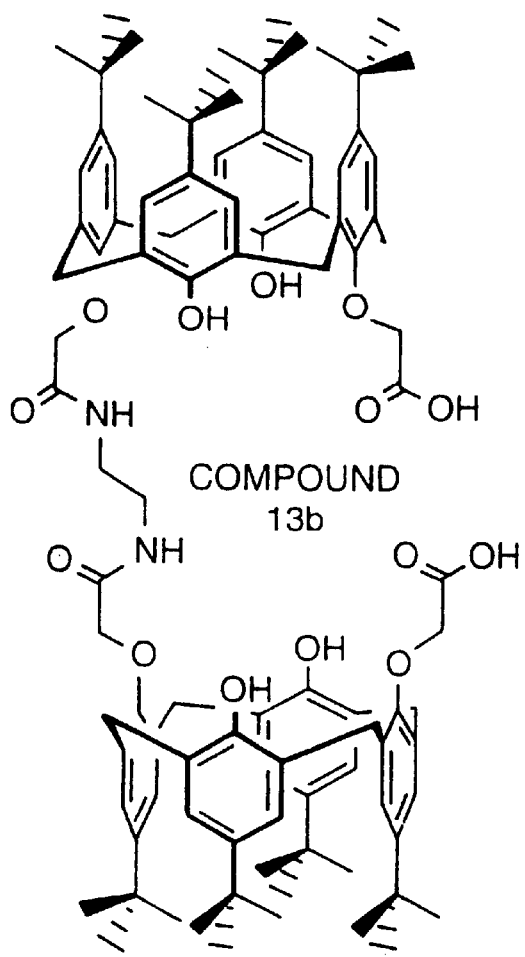
FIG. 10 shows a calixarene dimer (designated 13b) according to the present invention.
Figure 11:
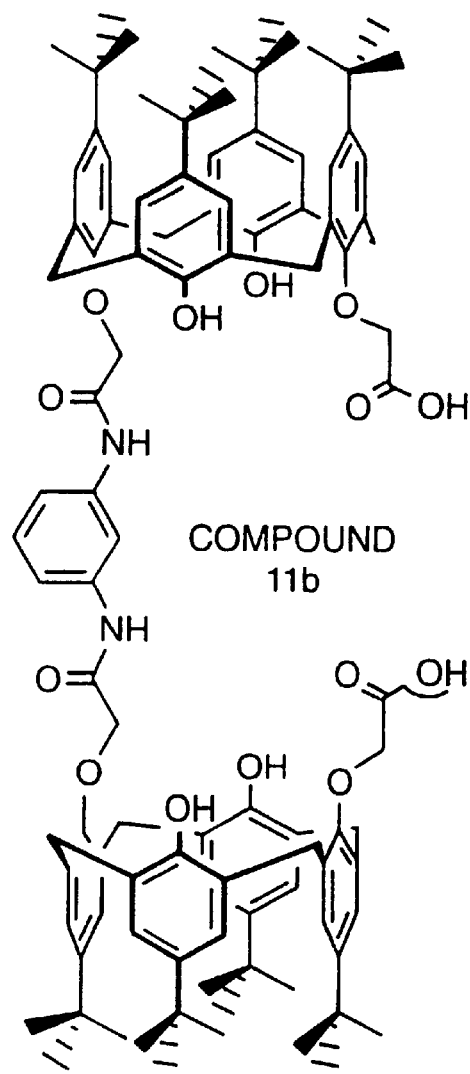
FIG. 11 shows a calixarene dimer (designated 11b) according to the present invention, having an aryl spacer group between the Nitrogen atoms of the two amide groups.

Compound 13b (FIG. 10) was prepared in order to mimic the calixarene/Lanthanide complex of FIG. 8. The dimer did not complex $La^{3+}$ at pH 6, a more alkaline pH (i.e. pH 9) being required to quantitatively extract La. This is possibly because steric hindrance may reduce La's ability to compete with protons for oxygen coordination sites at low pHs. Metal:Ligand ratios in the solvent extracted complex were determined to be 0.54 i.e. for every 2 La:dimer. This suggests that all six ionizable —OH groups are dissociated forming a complex similar to that in FIG. 6. La, in the presence of Lu and U, at pH 9 is preferentially extracted.

By contrast, U is quantitatively extracted at pH 6 (unlike La). The metal:Ligand ratio at pH 6 was approximately 1:1 suggesting a different complex is forming to that formed by La at higher pH.

Compound 11b (FIG. 11) was prepared in order to optimise the bridging group between the calixarenes for U extraction. The meta-di-phenylamine linkage restricts the two calixarene halves such that the carboxyl groups are close to each other. This is the predicted conformation in the metal complex, unlike the conformation in free solution, wherein it is predicted that steric effects will mean that the halves are diametrically opposed around the bridging group. The compound extracted U much more efficiently at pH 9 than pH 6 (80% rather than 20%). This is in contrast to Compound 13b above. The more alkaline operating conditions of 11b may be more applicable to some clean up applications.

In Compound 10 (FIG. 12) the carboxy group of the calixarenes has been protected with benzyl alcohol. No U extraction occurred at pH 6 (as with Compound 13b). Compound 11 (FIG. 13) is similar to compound 10 but was generated using a different diamine. Again no extraction of U occurred at pH 6. Significant extraction of U and Hg occurred at pH 9 notwithstanding the presence of the protecting group. This implies that a deprotonated carboxy group is not necessary for completing U or Hg, but that the phenolic groups (deprotonated at high pH) are crucial to extraction. Compound 11a is protected with as an ethyl ester, and has the di-phenylamine linkage of compound 13b. Again no U extraction occurred at pH 6.

It is clear that the pH dependent specificity of the dimeric compounds above give them utility in the selective extraction of different metals.

Example 11

The acid-amide was physisorbed and immobilised onto polystyrene divinyl benzene beads in an inert diluent. Solutions containing U were passed through a chromatography column containing the beads at various different pHs at a flow rate of approximately 2 mls/min. A control experiment was carried out with blank beads. The results are shown Table 2. As can be seen, above pH 2 extraction of U occurred, reaching 100% at pH 3. The kinetics were fast enough to absorb the U from the relatively fast moving mobile phase.

TABLE 2

| | Extraction Efficiency | |
|---|---|---|
| pH | Acid-amide resin | Blank |
| 1 | 2 | 10 |
| 2 | 37 | 34 |
| 3 | 100 | 20 |
| 4 | 100 | 21 |
| 6 | 93 | 21 |
| 9 | 34 | 0 |

Example 12

Synthesis of acid-amide (designated A954 below).
Synthetic Scheme

A954 was synthesised using the route shown in FIG. 15. The bis-ester (A955) was synthesised following the literature method of Collins et al (1991) J. Chem Soc., Perkin Trans.,1, 3137. Reaction of p-tert-Butylcalix[4] arene with 2 equivalents of ethyl bromoacetate in acetone with potassium carbonate (as base) gave the bis-ester in good yield. This was mono-deprotected using 1 equivalent of potassium hydroxide in ethanol. Although the product contained traces of both bis-ester and bis-acid as impurity, it was used without further purification and the impurities removed in subsequent steps. Overnight reflux with thionyl chloride in dichloromethane gave the acyl chloride which was reacted immediately with excess diethylamine (in dichloromethane with triethylamine present) to give the calixarene amide-ester (A953) in 72% overall yield. Finally, deprotection of the ester group using potassium hydroxide in ethanol gave the desired acid-amide (A954).
Detailed Synthesis NMR data was compiled after each step, but is shown only for the final product.

A955: p-tert-Butylcalix[4] arene 10 g, 0.015 mol) and anhydrous potassium carbonate (4.68 g, 0.34 mol) were slurried in dry acetone (distilled from $CaSO_4$) for 2 hours. Ethylbromoacetate (5.15 g, 0.031 mol) was added. and the mixture stirred under nitrogen for three days. It was then filtered, the solvent distilled off and the residue dried under vacuum. It was then slurried with cold ethanol to form a white powder and collected by filtration. This solid was washed with a further quantity of cold ethanol and dried under vacuum. Yield 8.97 g (73%).

951: bis-ester A955 (8.0 g, 9.76 mmol) was slurried in ethanol (600 ml). Potassium hydroxide (85% AR, 0.55 g, 9.76 mmol) added and the mixture heated to reflux for 1–2 hours. On cooling the ethanol was reduced in volume (to 50–100 ml) and 1 M HCl added to precipitate the product. This was collected by filtration and washed with water(50 ml). The product was dried under vacuum.

Yield 6.95 g (90%) (Found: C, 73.84; H, 7.42; required C, 75.72; H. 7.62%);

A953: acid-ester 951 (5.0 g, 6.31 mmol) was refluxed overnight with thionyl chloride (3.5 ml) in dry dichloromethane (100 ml). The solvent was then removed by distillation and the oily yellow residue dried under vacuum. Additions of dichloromethane (4–5 ml) were necessary to help azeotrope off the last traces of thionyl chloride. When dry, the product was a glassy off-white solid. The acyl chloride ester was then dissolved in dry dichloromethane (50 ml). To this solution was added dropwise, a solution containing dry diethylamine (dried over KOH) (0.98 ml, 9.45 mmol) and dry diethylamine (dried over CaH$_2$) (0.87 ml, 6.31 mmol) in dry dichloromethane (50 ml) over 30 minutes. After stirring overnight at room temperature, the solution was transferred to a dropping funnel and washed with 1 M HCl (50 ml) and then water (50 ml). It was then dried over MgSO4, filtered and the solvent removed in vacuo. The crude product was purified by column chromatography on silica (Kieselgehl) using dichloromethane/methanol (98:2) eluent.

Yield 3.86 g (72%) (Found: C, 74.83; H, 8.13; N, 2.12. required C,74.87, H, 8.72, N, 1.61%)

954: amide-ester, A953, (2.20 g, 2.48 mmol) was dissolved in ethanol(150 ml) and potassium hydroxide (0.28 g, 4.96 mmol) added. The resulting solution was then refluxed for 2 hours. After cooling to room temperature, the volume of the solution was reduced to ca. 25 ml by rotary evaporation. Addition of 1 M HCl gave a white precipitate which was collected by filtration and washed with water. It was then dissolved in dichloromethane (30 ml). washed with 1 M HCl (30 ml) water (30 ml) and then dried over MgSO4. The solvent was removed in vacuo to give a foamy white solid. It was converted to a powder by dissolving in a minimum of dichloromethane and adding hexane (30–40 ml)—evaporation to dryness gave a white solid. Yield 2.06 g (97%) (Found: C, 75.24; H, 8.77; N, 1.97. required C, 75.33, H,8.51, N, 1.69%).

NMR data (300 MHz, CDCl3) 1.07 (9H, s, —Bu). 1.11 (9H, s, —Bu), 1.25 (18H, s, —Bu), 1.25 (3H, t, —CH$_3$), 3.38 (2H, d, Ar—CH$_2$—Ar), 3.38 (2H, q, —NCH$_2$—), 3.42 (2H, d, J=13.0 Hz, Ar—CH$_2$—Ar), 3.55 (2H, q, —NCH$_2$—), 4.22 (2H, d, J=13.0 Hz, Ar—CH$_2$—Ar), 4.30 (2H, d, J=13.3 Hz, Ar—CH$_2$—Ar). 4.64 (2H, s, —OCH$_2$CO—), 4.78 (2H, s, —OCH$_2$CO—), 6.93 (2H, s, Ar), 6.99 (2H, s, Ar), 7.03 (2H, d, Ar), 7.06 (2H, d, Ar), 8.90 (2H, br s, —OH); (75.42 MHz, CDCl3) 13.02, 14.36, 31.12, 31.68, 32.17, 32.35, 33.91, 34.05, 34.16, 40.78, 41.20, 72.44, 73.29, 125.24, 125.55, 126.10, 127.21, 128.29, 132.71, 132.94, 142.32, 147.49, 148.51, 149.76, 150.11, 150.21, 166.71, 170.44; FAB m.s., m/z 864 (M+2Na$^+$—H., 18%), 842 (M+Na$^+$, 100), 820 (M+, 10).

It should be noted that the synthesis of other calixarenes falling within the claims of the present application may be readily achieved by the skilled person in the light of the disclosure of the present document, particularly in combination with the common general knowledge of the skilled person, as evidenced for example by the teaching and references of EP 0 432 989.

954/Metal Complex Synthesis

To prepare Ln (NO$_3$)$_3$.nDMSO, n=3,4 Ln$_2$O$_5$ was dissolved in a minimum of nitric acid (fast exothermic process for large Ln, slow process for small Ln). To the resulting solution was added a 5–6 fold excess of dimethyl sulphoxide. Ethanol and then diethyl ether were then added to precipitate the product. Occasionally, when the product oiled out, it was necessary to decant the mother liquor, add more ethanol/diethyl ether and then scratch with a glass rod. The product was then collected by filtration, redissolved in DMSO and precipitated with ethanol/ether. The final product was collected by filtration and dried under vacuum. All DMSO solvates gave elemental analyses in accordance with their proposed structures.

A simpler method involved the use of Ln (NO$_3$)$_3$ penta and hexahydrates instead of the oxide. In this case the salt was twice dissolved in DMSO and precipitated with ethanol and diethyl ether.

The calixarene acid-amide A954 (0.0189 g, 0.023 mmol) was dissolved in 1 ml DMF. To this solution was added Ln (NO$_3$)$_3$.nDMSO (n=3 or 4, 0.025 mmol) also in 1 ml DMF. After the further addition of 30 microlitres of triethylamine (excess), the solution was immediately filtered and left to stand. As mentioned earlier, the larger lanthanides precipitated quite quickly from solution whereas the smaller ones took considerably longer. The precipitated complex was then collected by filtration and washed with a minimum of cold ethanol (ca. 0.5 ml) and dried under vacuum. Attempts were made to recrystallise these complexes from dichloromethane/ethanol. This typically involved dissolving the complex in dichloromethane (1.5 ml) and then adding ethanol (1 ml). After filtering, the solution was left to slowly evaporate.

For the larger lanthanides (La-Eu), the complex precipitated fairly quickly from solution, and was then recrystallised from dichloromethane/ethanol. In case of the Eu and Sm complexes, crystals suitable for X-ray crystallographic analysis were isolated.

Precipitated from DMF/NEt:Sm complex of A954; Found: C, 64.0; H, 7.2; N, 3.3. required C, 64.3, H, 7.5, N, 3.7%.

Eu complex of A954; Found: C, 63.9; H, 7.1; N, 3.4. required C, 64.2, H, 7.5, N, 3.7%.

Recrystallised from ethanol/dichloromethane:

Eu complex of A954; Found: C, 65.6; H, 7.5; N, 2.8. required C, 65.6, H, 7.9, N, 2.6%.

The smaller lanthanide complexes (Lu) less readily precipitated from DMF solution than the larger ones described above, instead crystallising out only after a period of weeks.

Example 13

Synthesis of azacrown-acid calix[4]arenes

In attempt to form discrete monomeric complexes across the Lanthanide series, the azacrown-acid calix[4]arenes A957 and A959 (FIG. 16) were prepared with the idea that the extra O-donor sites present would more easily satisfy the normal 8–10 coordination sphere of the larger Lanthanides.

The synthetic scheme used in the synthesis of the simpler acid-amide (A954) was also applied in the synthesis of the azacrownacidcalix[4]arenes, FIG. 15. For the final deprotection step, in order to eliminate the possibility of isolating alkali-metal complexes of the product, potassium hydroxide was used as base in the deprotection of the N-aza-15-crown-5 ligand and sodium hydroxide in the case of theN-aza-18-crown-6 ligand.

Isolation of Complexes

Preliminary work was also begun on the isolation of the Lanthanide complexes of these ligands, the majority of this involving theN-aza-15-crown-5 analogue only. The same methods were applied as for the simpler acid-amide (A954) and, in general, the same observations made. Again the larger Ln cations formed complexes which readily precipitated from DMF solution. Attempts at recrystallisation of these complexes from dichloromethane/ethanol again yielded X-ray crystallographic quality crystals of the Sm complex. Disappointingly, however, the anticipated monomeric complex was not formed. Instead, a similar dimeric structure was adopted with the aza-crown folding away and not coordinating to Sm.

Example 14

U.V. Spectra

The observed maxima for the 954 acid-amide are listed in Table 3 together with the corresponding values for selected complexes. The extinction values given are approximate only. Given that the sample sizes measured were only about 1 mg, weighing errors could easily account for apparent differences in absorption between related species.

Example 15

Synthesis of acid-amide dimer. The dimers of Example 10 were prepared by methods analogous to those above. In the case of 11a, compound A952 (FIG. 15) was prepared as described above. Two molecules of A952 were dimerised with m-phenylenediamine in dichloromethane and triethylamine. The yield was 68%. Compound 11b was prepared from 11a by regenerating the carboxy group with potassium hydroxide in ethanol. The yield was 90%. The other dimers were prepared using different diamines (e.g. 1,2-di-(methylamino)ethane for 11 and 13b). Other protecting groups can be added either as alcohols to the deprotected acid group, or incorporated into the precursor e.g. by substituting the ethylbromoacetate used to prepare A955 in Example 12 with a bromylated benzyl ester. The diamine synthetic route is flexible in that a wide variety of spacer groups may be introduced between the calixarene halves, allowing factors such as chain length, coordination etc. to be assessed.

TABLE 3

| Compound/complex | Wavelength (nm) | Maxima $cm^{-1}M^{-1}$ |
|---|---|---|
| 954 | 228 | 36000 |
|  | 282 | 9500 |
| 954/La | 228 | 50000 |
|  | 260 (sh) | 15000 |
|  | 307 | 9400 |
| 954/Sm | 228 | 46000 |
|  | 260 (sh) | 13000 |
|  | 307 | 9600 |
| 954/Eu | 228 | 48000 |
|  | 260 (sh) | 15000 |
|  | 306 | 9700 |

Example 16 synthesis of the ester-thioamide A960 A960 was synthesised using the route shown in FIG. 17. The precursor A953 was prepared by the route shown in FIG. 15 and Example 12. Lawesson's reagent (0.49 g, 1.2 mmol) was added to a solution of ester-amide A953 (1.0 g, 1.17 mmol) in toluene (20 cm³) and the mixture was heated at 80° C. for 4 hr. After cooling to room temperature, the toluene was removed under reduced pressure to give a yellow oil. This oil was dissolved in acetonitrile (15 cm³) and filtered through an alumina pad. Dropwise addition of water to the filtrate afforded a yellow precipitate, which was removed by filtration and recrystallised from dichloromethane-ethanol to afford A960 as yellow prismatic crystals (095 g, 94%). The structure of this compound was confirmed by NMR, mass spectrometry and X-ray crystallography.

Example 17 synthesis of the acid-thioamide A961 A961 was synthesised using the route shown in FIG. 17. The ester-thioamide A960 was synthesised by the route shown in FIG. 17 and Example 16. Potassium hydroxide (0.036 g, 0.65 mmol) was added to a solution of ester-thioamide A960 (0.5 g, 0.58 mmol) in ethanol (25 cm³) and the solution heated under reflux for 2 hr. The ethanol was reduced in volume to approximately 5 cm³ and 1 M HCl added to precipitate A961 as a pale yellow powder which was recrystallised from dichloromethane-hexane (0.41 g, 85%). The structure of this compound was confirmed by NMR and mass spectrometry.

Example 18

FIG. 18 shows the ability of the calixarenes A954, A960 and A961 to extract cadmium ions at pH 9.4. Equal volumes of aqueous cadmium cyanide solution (pH 9.4, $[Cd^{2+}]$= 0.238 mMolar) and a solution of a calixarene in dichloromethane were mixed for 15 minutes by stirring. The aqueous and organic phases were then allowed to separate for about 30 minutes. The aqueous layer (Aq1) was then removed, and the organic layer was washed with a nitric acid blank (pH 9.4). The aqueous and organic layers were allowed to separate for about 30 minutes, and the aqueous layer was then removed (Aq2). Aq1 contained the cadmium ions that had not been extracted by the calixarenes, whereas Aq2 contained the cadmium ions that had been extracted by the calixarenes (and subsequently liberated by acidification of the organic layer). Aq1 and Aq2 were made up to known volumes. ICP AES (inductively coupled plasma atomic emission spectroscopy) was then used to determine the concentration of cadmium ions in the solutions. These figures can readily be used to determine the percentage extraction of cadmium for a given ratio of concentration of calixarene:cadmium.

FIG. 18 indicates that both the acid-thioamide A961 and the ester-thioamide A960 are capable of extracting cadmium ions from solution. The order of efficiency of extraction is acid-thioamide, A961>acid-amide, A954>ester-thioamide, A960. The order can be explained by the fact that both A961 and A954 have a proton that can be readily lost from the acid substituent. The resulting anion will attract and retain cadmium ions more effectively than the (usually uncharged) ester group The acid-thioamide (A961) forms complexes with cadmium more readily than the acid-amide (A954) because the S atom in A961 is a "softer" atom than the 0 atom in A954, and is thus more polarisable and thus is more likely to form a complex with a $Cd^{2+}$ ion, which is itself a "soft" ion.

What is claimed is:
1. A calixarene dimer comprising a calixarene of formula (I)

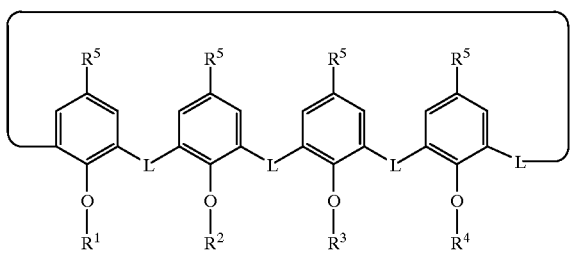

formula (I)

wherein:
L is [—$CH_2$—] or [—O—$CH_2$—O—] and is the same or different between each aryl group;
$R^5$ is H, halogen, or is a $C_1$–$C_{10}$ aliphatic hydrocarbyl group, $C_6$–$C_{20}$ aryl group or a $C_6$–$C_{20}$ hydrocarbylaryl group, any of which is optionally substituted by one or more halo or oxo groups or is interrupted by one or more oxo groups, and $R^5$ is the same or different on each aryl group;
$R^1$ is a carboxy group which is or is not protonated or protected;
two groups out of $R^2$, $R^3$ and $R^4$ are H; and
the one group out of $R^2$, $R^3$ and $R^4$ which is not H is an amide group of formula (II)

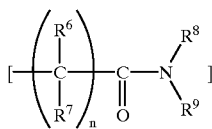

formula (II)

wherein n is 1, 2 or 3 and $R^6$ and $R^7$ are H, halogen or a $C_1$–$C_{10}$ aliphatic hydrocarbyl group, and are the same or different on each carbon, and wherein $R^8$ and $R^9$, which is the same or different, are H or a $C_1$–$C_{10}$ aliphatic hydrocarbyl group which is substituted by one or more halo groups, or is a cycloaliphatic ring formed by $R^8$ and $R^9$ together wherein one of the $R^8$ and $R^9$ groups is conjugated to a second calixarene.

2. The dimer as claimed in claim 1 comprising two calixarenes of formula (I) wherein the $R^8$ or $R^9$ group of one calixarene is conjugated to the $R^8$ or $R^9$ group of the other calixarene, optionally through a spacer group $R^{11}$, the optional spacer $R^{11}$ being a $C_1$–$C_6$ aliphatic hydrocarbyl group, or a $C_6$–$C_{10}$ aryl group, or a $C_6$–$C_{16}$ hydrocarbylaryl group any of which is optionally substituted by one or more halo or oxo groups or is interrupted by one or more oxo groups.

3. The dimer as claimed in claim 2 wherein there is a 1, 2, 3 or 4 atom chain between the nitrogen atoms of the two amide groups.

4. The process for preparing a dimer as claimed in claim 2 comprising reacting two equivalents of a calixarene bearing an acyl chloride substituent with 1 equivalent of diamine.

5. A method of sequestering metals comprising contacting metals with a calixarene dimer as claimed in claim 2.

6. The method as claimed in claim 5 wherein the method is carried out at a pH of between 2 and 11.

7. The method as claimed in claim 5 wherein the pH at which the method is carried out is buffered.

8. A method of sequestering metals comprising the steps of:

(i) dissolving a calixarene dimer of claim 1 in an hydrophobic organic solvent;

(ii) mixing the organic solvent with an aqueous phase containing metal ions;

(iii) agitating the organic solvent and aqueous phase together; and (iv) recovering the metal from the organic phase.

9. The method as claimed in claim 5 or 8 wherein the metal is selected from a Lanthanide, U, Hg, Am, Pb, Sr, Bi and Y.

* * * * *